United States Patent [19]

Hagen et al.

[11] Patent Number: 5,281,705
[45] Date of Patent: Jan. 25, 1994

[54] METHOD FOR MAKING HIGH BULK DENSITY CRYSTALLINE 3-CYANO-2-MORPHOLINO-5-(PYRID-4YL)-PYRIDINE

[75] Inventors: Volker Hagen; Günter Reck; Brigitte Gentsch, all of Berlin; Hans-Joachim Heidrich, Dresden; Hans-Joachim Jänsch, Radebeul; Ingrid Wielop, Radebeul; Dieter Lohmann, Radebeul, all of German Democratic Rep.

[73] Assignee: Arzneimittelwerk Dresden GmbH, Radebeul, German Democratic Rep.

[21] Appl. No.: 971,297

[22] Filed: Nov. 4, 1992

Related U.S. Application Data

[62] Division of Ser. No. 665,681, Mar. 7, 1991, Pat. No. 5,204,464.

[30] Foreign Application Priority Data

Mar. 9, 1990 [DD] German Democratic Rep. ... 338544

[51] Int. Cl.$^5$ .......................................... C07D 413/14
[52] U.S. Cl. .................................................... 544/124
[58] Field of Search ........................................ 544/124

[56] References Cited

PUBLICATIONS

Hagen et al., Chemical Abstracts, vol. 107 (1987) No. 7074p.

Primary Examiner—Robert W. Ramsuer
Attorney, Agent, or Firm—Schweitzer Cornman & Gross

[57] ABSTRACT

A method for preparing high bulk density crystalline 3-cyano-2-morpholino-5-(pyrid-4-yl)-pyridine which comprises precipitating a high bulk density crystalline 3-cyano-2-morpholino-5-(pyrid-4-yl)-pyridine from a starting material that is (a) a solution in an inorganic or organic acid, and precipitating with a base, or
(b) a solution in a chlorinated hydrocarbon, and precipitating with an aliphatic hydrocarbon, or
(c) from an aliphatic ester of an aliphatic carboxylic acid and an aliphatic alcohol.

The compact, crystalline 3-cyano-2-morpholino-5-(pyrid-4-yl)-pyridine, so obtained, has a bulk density of from about 220 to about 360 g/l and is most suitable for pharmaceutical preparations.

16 Claims, No Drawings

METHOD FOR MAKING HIGH BULK DENSITY CRYSTALLINE 3-CYANO-2-MORPHOLINO-5-(PYRID-4YL)-PYRIDINE

This is a divisional application of U.S. Ser. No. 665,681, filed on Mar. 7, 1991, now U.S. Pat. No. 5,204,464.

FIELD OF THE INVENTION

The present invention relates to compact, high bulk density crystalline 3-cyano-2-morpholino-5-(pyrid-4-yl)-pyridine, and to methods for its preparation. 3-Cyano-2-morpholino-5-(pyrid-4-yl)-pyridine can be used as a cardiotonic drug, which also has vasodilator properties.

BACKGROUND OF THE INVENTION

The preparation of 3-cyano-2-morpholino-5-(pyrid-4-yl)-pyridine, by reacting 3-cyano-2-chloro-5-(pyrid-4-yl)-pyridine with excess morpholine and recrystallizing the resulting crude product from ethanol is known from East German patent No. 236,729, Example 7; and European patent No. 200,024 A. The recrystallized product is obtained as thin, feltlike needles, which have only a low bulk density of 150 g/l and create considerable difficulties during pharmaceutical processing.

DESCRIPTION OF THE INVENTION

It is an object of the invention to provide a compact, high bulk density crystalline 3-cyano-2-morpholino-5-(pyrid-4-yl)-pyridine, and methods for its preparation.

Pursuant to the invention, this objective is accomplished in that 3-cyano-2-morpholino-5-(pyrid-4-yl)-pyridine is either
(a) dissolved in an acid and is then precipitated with a base from the acidic solution, or
(b) dissolved in a chlorinated hydrocarbon and is then precipitated by adding an aliphatic hydrocarbon to the solution, or
(c) recrystallized from an aliphatic ester of an aliphatic carboxylic acid, and an aliphatic alcohol.

In accordance with the present invention, it is possible to use the 3-cyano-2-morpholino-5-(pyrid-4-yl)-pyridine as a crude, or purified starting material.

In an embodiment of the present invention a solution of 3-cyano-2-morpholino-5-(pyrid-4-yl)-pyridine is treated with an adsorbent, such as activated charcoal or silica gel before the precipitation and/or recrystallization. This is particularly advantageous when crude 3-cyano-2-morpholino-5-(pyrid-4-yl)-pyridine is used as the starting material.

If the 3-cyano-2-morpholino-5-(pyrid-4-yl)-pyridine is to be precipitated from its acidic solutions with bases according to the process variant (a), this is suitably carried out at a temperature of from about 15° C. to about 40° C., suitably at about 30° C. Inorganic as well as organic acids are suitable for carrying out the process variant (a) of the present invention, and solutions of alkali hydroxide ammonia, or alkali carbonate can be used as the base. Suitably the 3-cyano-2-morpholino-5-(pyrid-4-yl)-pyridine is precipitated from a solution in a mineral acid as the salt of the mineral acid by the addition of further mineral acid, separating this salt from the aqueous phase, dissolving it in water and precipitating it again with a base, after an optional treatment with an adsorbent.

According to the process variant (b) of the present invention, the 3-cyano-2-morpholino-5-(pyrid-4-yl)-pyridine is precipitated from a chlorinated hydrocarbon by an aliphatic hydrocarbon. A chlorinated hydrocarbon such as chloroform, or dichloromethane can suitably be employed for this purpose. A $C_{5-10}$ hydrocarbon or mixtures of such hydrocarbons, such as hexane, or petroleum ether, can be used as the aliphatic hydrocarbon.

In recrystallization according to the process variant (c) of the present invention, suitably the precipitation is carried out by cooling rapidly and intensively especially while stirring. Esters of $C_{1-3}$ aliphatic carboxylic acids and $C_{1-4}$ aliphatic alcohols are particularly suitable. Suitably, the ester is butyl acetate.

Depending on the particular reaction conditions, the high bulk density crystalline 3-cyano-2-morpholino-5-(pyrid-4-yl)-pyridine, produced in accordance with the present invention, is obtained in three previously unknown crystalline modifications. These crystalline modifications are referred to here as the $\alpha$, the $\gamma$ and the $\epsilon$ form.

None of the preparations of the three crystalline modifications can be attributed to a particular process variant (a), (b), or (c). Rather, even slight changes within the aforementioned variants such as changing the acid and/or the base in the case of variant (a), or changing the chlorinated hydrocarbon and/or the aliphatic hydrocarbon in the case of variant (b), or also changing only the cooling process and the crystallization rate, will lead to different crystalline modifications or mixtures of the same, as illustrated by the examples.

The particular crystalline modification is of no significance. The important fact according to the present invention is that regardless of the crystalline modification or mixture of modifications that are obtained pursuant to the present invention, the result is always a compact, crystalline 3-cyano-2-morpholino-5-(pyrid-4-yl)-pyridine, with a bulk density of from about 220 to about 360 g/l, which is high in comparison to that obtained by known methods. This crystalline material can be processed well in combination with pharmaceutical carriers and auxiliaries, into high quality into pharmaceutical preparations.

The data that are of importance for the identification of the $\alpha$, $\gamma$ and $\epsilon$ modifications of the 3-cyano-2-morpholino-5-(pyrid-4-yl)-pyridine, are described in the following Tables 1 to 4.

The crystallographic data of the $\alpha$, and $\gamma$ modifications of this compound, determined by X-ray diffraction investigations, are given in Table 1.

TABLE 1

| | Crystal Data | |
|---|---|---|
| | I-$\alpha$ | I-$\gamma$ |
| Empirical formula | $C_{15}H_{14}N_4O$ | $C_{15}H_{14}N_4O$ |
| Crystalline system | monoclinic | triclinic |
| Space Group | $P2_1/n$ | $P\bar{1}$ |
| Lattice constants: | | |
| a | 19.495 (11) Å | 6.657 (2) Å |
| b | 4.697 (2) Å | 8.428 (2) Å |
| c | 28.509 (26) Å | 12.867 (5) Å |
| $\alpha$ | 90° | 103.64 (3)° |
| $\beta$ | 92.01 (7)° | 99.11 (2)° |
| | 90° | 102.57 (2)° |
| Number of formula units in the elementary cell | 8 | 2 |
| $D_{calc.}$ | 1.356 g/cc | 1.325 g/cc |

The following formula shows the molecule of I with the numbering of the atoms.

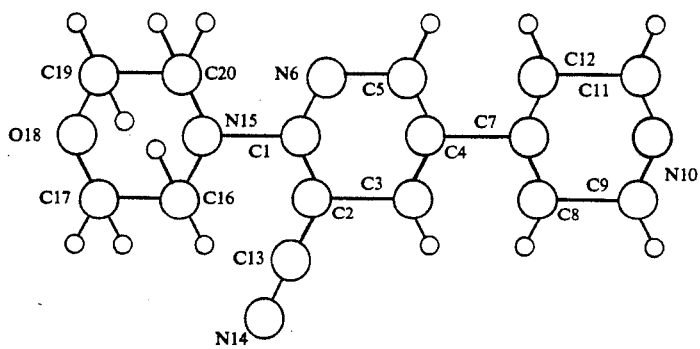

The following Tables 2 and 3 contain the atomic coordinates of I-α and I-γ. The powder diagrams (d values and relative intensities) of I-α and I-γ, calculated from the single crystal structure data, as well as the experimental powder diagram of I-ε, determined by the Guinier technique, are shown in Table 4.

TABLE 2

| Atomic Coordinates (×10⁴) of I-α | | | | | | | |
|---|---|---|---|---|---|---|---|
| Molecule A | | | | Molecule B | | | |
| Atom | x/a | y/b | z/c | Atom | x/a | y/b | z/c |
| O18 | 1072(2) | 6942(10) | 2563(2) | O18 | 3687(2) | −3848(10) | 1038(2) |
| N6 | 1998(2) | 2304(10) | 1254(2) | N6 | 5964(3) | 5622(10) | 1732(2) |
| N10 | 2245(3) | −5836(10) | −5836(2) | N10 | 9203(3) | −8442(10) | 1959(2) |
| N14 | −40(3) | 7009(10) | 649(2) | N14 | 5805(4) | −10518(20) | 249(3) |
| N15 | 1296(3) | 5398(10) | 1626(2) | N15 | 5034(3) | −5898(10) | 1232(2) |
| C1 | 1429(3) | 3818(10) | 1240(2) | C1 | 5689(3) | −6590(10) | 1325(2) |
| C2 | 967(3) | 3665(10) | 845(2) | C2 | 6130(3) | −8222(10) | 1032(2) |
| C3 | 1142(3) | 1833(10) | 477(2) | C3 | 6783(3) | −8746(10) | 1177(2) |
| C4 | 1724(3) | 203(10) | 500(2) | C4 | 7066(3) | −7673(10) | 1583(2) |
| C5 | 2153(3) | 596(10) | 896(2) | C5 | 6606(3) | −6161(20) | 1857(2) |
| C7 | 1913(3) | −1814(10) | 127(2) | C7 | 7788(3) | −8019(10) | 1730(2) |
| C8 | 1449(3) | −2592(10) | −227(2) | C8 | 8222(3) | −9804(20) | 1491(2) |
| C9 | 1654(3) | −4549(10) | −563(2) | C9 | 8887(4) | −9943(20) | 1619(3) |
| C11 | 2710(3) | −5034(20) | −229(2) | C11 | 8770(4) | −6769(20) | 2201(3) |
| C12 | 2544(4) | −3078(10) | 122(2) | C12 | 8097(3) | −6464(20) | 2090(2) |
| C13 | 413(3) | 5536(10) | 756(2) | C13 | 5913(4) | −9482(20) | 598(3) |
| C16 | 664(3) | 6593(20) | 1762(2) | C16 | 4714(4) | −5948(20) | 766(3) |
| C17 | 526(3) | 6019(20) | 2263(2) | C17 | 3994(4) | −5914(20) | 755(3) |
| C19 | 1667(3) | 5528(20) | 2441(2) | C19 | 3948(4) | −4054(20) | 1491(3) |
| C20 | 1873(3) | 6195(10) | 1959(2) | C20 | 4691(3) | −3912(20) | 1539(2) |

TABLE 3

| Atomic Coordinates (×10⁴) of I-γ | | | | | | | |
|---|---|---|---|---|---|---|---|
| Molecule A | | | | Molecule B | | | |
| Atom | x/a | y/b | z/c | Atom | x/a | y/b | z/c |
| O18 | 3544(3) | −7776(2) | 63(1) | C7 | 6578(3) | 685(2) | 6301(1) |
| N6 | 6737(2) | −3377(2) | 3553(1) | C8 | 5130(3) | −191(3) | 6883(2) |
| N10 | 7822(3) | 1869(2) | 8325(1) | C9 | 5813(4) | 1063(3) | 7870(2) |
| N14 | −270(3) | −6504(3) | 3528(2) | C11 | 9208(4) | 1392(3) | 7770(2) |
| N15 | 4319(2) | −5482(2) | 2162(1) | C12 | 8687(3) | 144(3) | 6783(2) |
| C1 | 4762(3) | −4386(2) | 3185(1) | C13 | 1304(3) | −5538(2) | 3656(2) |
| C2 | 3311(3) | −4322(2) | 3881(1) | C16 | 2236(3) | −6032(3) | 1414(5) |
| C3 | 3906(3) | −3112(2) | 4894(1) | C17 | 1946(4) | −7774(3) | 678(2) |
| C4 | 5909(3) | −2016(2) | 5246(1) | C19 | 5560(4) | −7284(3) | 791(2) |
| C5 | 7255(3) | −2272(3) | 4538(1) | C20 | 6002(3) | −5535(3) | 1553(2) |

TABLE 4

| Experimental and Calculated Powder Diagrams | | | | | |
|---|---|---|---|---|---|
| I-α | | I-γ | | I-ε | |
| d(A) | Intens. | d(A) | Intens. | d(A) | Intens. |
| 14.24 | 22 | 12.20 | 42 | 9.36 | 30 |
| 9.74 | 14 | 7.89 | 11 | 7.77 | 62 |
| 8.66 | 9 | 6.33 | 64 | 7.12 | 41 |
| 8.18 | 22 | 6.21 | 41 | 6.50 | 100 |
| 7.91 | 84 | 5.74 | 18 | 5.78 | 73 |
| 7.12 | 43 | 5.17 | 20 | 5.41 | 12 |
| 6.38 | 10 | 4.62 | 5 | 5.24 | 61 |
| 6.28 | 100 | 4.25 | 32 | 4.64 | 40 |
| 5.66 | 21 | 4.17 | 13 | 4.23 | 60 |
| 5.52 | 55 | 4.11 | 23 | 4.13 | 23 |
| 5.43 | 10 | 3.84 | 67 | 4.03 | 10 |
| 4.87 | 43 | 3.82 | 16 | 3.96 | 11 |
| 4.64 | 20 | 3.59 | 10 | 3.88 | 85 |
| 4.56 | 14 | 3.47 | 100 | 3.80 | 14 |
| 4.50 | 20 | 3.33 | 8 | 3.66 | 43 |
| 4.46 | 27 | 3.15 | 14 | 3.58 | 22 |

TABLE 4-continued

| Experimental and Calculated Powder Diagrams | | | | | |
|---|---|---|---|---|---|
| I-α | | I-γ | | I-ε | |
| d(A) | Intens. | d(A) | Intens. | d(A) | Intens. |
| 4.35 | 8 | | | 3.50 | 17 |
| 4.21 | 22 | | | 3.42 | 80 |
| 4.12 | 9 | | | 3.31 | 41 |
| 4.07 | 18 | | | | |
| 4.01 | 71 | | | | |
| 3.88 | 55 | | | | |
| 3.83 | 33 | | | | |
| 3.70 | 30 | | | | |
| 3.66 | 43 | | | | |
| 3.61 | 15 | | | | |
| 3.58 | 9 | | | | |
| 3.56 | 30 | | | | |
| 3.48 | 6 | | | | |
| 3.42 | 34 | | | | |

The following examples further illustrate the present invention.

EXAMPLE 1

(a) 3-Cyano-2-morpholino-5-(pyrid-4-yl)-pyridine hydrochloride monohydrate 5.0 kg 3-cyano-2-morpholino-5-(pyrid-4-yl)-pyridine is mixed with 25 l water and 2.0 l technical grade hydrochloric acid and is then heated to about 50° C. 3.0 l hydrochloric acid is added to the yellow solution, which is then cooled. After crystallization, stirring is continued for a further 2 hours at temperatures below 20° C. The crystalline material is centrifuged off and washed with a mixture of 5.4 l water and 0.6 l hydrochloric acid. The yield is 5.3 kg (88% of the theoretical yield).

(b) 3-Cyano-2-morpholino-5-(pyrid-4yl)-pyridine (γ-modification)

5.3 kg 3-cyano-2-morpholino-5-(pyrid-4-yl)-pyridine hydrichloride monohydrate is suspended in 40 l water and the suspension is heated to 50° C. 0.5 kg activated charcoal is added and filtered off with suction after 15 minutes of stirring and washed with water. The filtrate is cooled to 30° C. While stirring, about 2.7 l concentrated sodium hydroxide solution is allowed to run in over a period of one hour at this temperature until pH 8-9. The crystalline material is centrifuged off and washed with total of 30 l water. The yield is 4.1 kg (93.2% of the theoretical yield), with a melting point of 126° C.-128° C. The bulk density of the material, after is was pulverized in a mortar, was about 360 g/l.

EXAMPLE 2

3-Cyano-2-morpholino-5-(pyrid-4-yl)-pyridine (γ-modification)

1 g purified 3-cyano-2-morpholino-5-(pyrid-4-yl)-pyridine of any modification is dissolved in 4 ml 1N HCl with heating to about 50° C. While being stirred, the material is precipitated at 30° C.-40° C. by being mixed with about 4 ml 1N NaOH. It is filtered off with suction, washed with water and dried at 110° C. The yield is 0.95 g (95% of the theoretical yield), with a melting point of 126° C.-128° C. The bulk density of the sample, after it was pulverized in a mortar, was about 360 g/l.

EXAMPLE 3

3-Cyano-2-morpholino-5-(pyrid-4-yl)-pyridine (α-modification)

4.0 kg prepurified 3-cyano-2-morpholino-5-(pyrid-4-yl)-pyridine is suspended in 40 l water, and 5.5 kg lactic acid is added. The temperature is raised to 50° C., 0.2 kg activated charcoal is added and filtered off after 15 minutes of stirring, and washed with warm water. After cooling to 30° C., 1.25 l concentrated sodium hydroxide solution is added until pH 8-9. Stirring is continued for a further hour, after which the crystalline material is centrifuged off, washed with a total of 30 l water and dried. The yield is 3.74 kg (93.5% of the theoretical yield) of slightly yellowish crystals, having a melting point of 127° C.-129° C. The bulk density of the sample, after it is pulverized in a mortar is about 230 g/l.

EXAMPLE 4

3-Cyano-2-morpholino-5-(pyrid-4-yl)-pyridine (mixture of γ- and ε-modifications)

100 g prepurified 3-cyano-2-morpholino-5-(pyrid-4-yl)-pyridine is suspended in 1.2 l water, to which 39 ml technical grade hydrochloric acid and 5 g of activated charcoal are added. The temperature is raised to 50° C. and the charcoal is filtered off once again. Concentrated ammonia solution (26 ml) is added drop-wise to the filtrate at about 30° C., stirring is continued for a further hour and the crystalline precipitate is filtered off with suction and washed 6 times with 50 ml water. The yield is 96.2 g (96.2% of the theoretical yield), and the melting point is (124) 127° C.-128° C. The bulk denisty of the sample, after it is pulverized in a mortar is about 300 g/l.

EXAMPLE 5

3-Cyano-2-morpholino-5-(pyrid-4-yl)-pyridine (α-modification)

3 g purified 3-cyano-2-morpholino-5-(pyrid-4-yl)-pyridine of any modification is dissolved in 5 ml CHCl$_3$ at a slightly elevated temperature and precipitated while stirring by the addition of 10 ml hexane. The precipitate is filtered off with suction and dried. The yield is 2.82 g (94% of the theoretical yield), and the melting point is 127° C.-128° C. The bulk density after it is pulverized in a mortar, is about 230 g/l.

EXAMPLE 6

3-Cyano-2-morpholino-5-(pyrid-4-yl)-pyridine (ε-modification)

1 g purified 3-cyano-2-morpholino-5-(pyrid-4-yl)-pyridine of any modification is dissolved in 4 ml CH$_2$Cl$_2$ at an elevated temperature and, while being stirred, precipitated by the addition of 5 ml hexane. The precipitate is filtered off with suction and dried. The yield is 0.97 g (97% of the theoretical yield), and having a melting point (124) of 127° C.-130° C. The bulk density of the sample after it is pulverized in a mortar is about 220 g/l.

EXAMPLE 7

3-Cyano-2-morpholino-5-(pyrid-4-yl)-pyridine (mixture of α-and ε-modifications)

125 g crude 3-cyano-2-morpholino-5-(pyrid-4-yl)-pyridine is refluxed with 1 l butyl acetate until dissolved. It is filtered hot and the solution is stirred for 10 minutes with heating with 10 g activated charcoal. The latter is filtered off hot. The filtrate is cooled in ice water with intensive stirring. The crystalline precipitate is filtered off with suction, washed with butyl acetate and methanol, dissolved once more in 900 ml butyl acetate at an elevated temperature, treated with 7 g of activated charcoal and filtered. The solution, which has a temperature of about 70° C., is caused to crystallize by intensive stirring and cooling. Stirring is subsequently continued for 2 hours at room temperature. After being kept in the refrigerator overnight, the crystalline precipitate is filtered off with suction, washed with methanol and dried at 110° C. The yield is 80 g (67% of the theoretical yield), and the melting point (124) is 128° C.-130° C. The bulk density of the sample, after it is pulverized in a mortar is about 245 g/l.

The yield can be increased by concentrating the mother liquors and recrystallizing the product obtained in the manner described.

EXAMPLE 8

3-Cyano-2-morpholino-5-(pyrid-4-yl)-pyridine (mixture of γ- and ε-modifications)

The procedure of Example 5 is followed. However, the precipitation is carried out by adding 60 ml 45% potassium carbonate solution dropwise at 30° C. The yield is 46.6 g (92.3% of the theoretical yield), and the melting point is 121° C.-123° C., and 126° C.-128° C. The bulk density of the sample after it is pulverized in a mortar is about 330 g/l.

We claim:

1. A method for preparing a crystalline 3-cyano-2-morpholino-5-(pyrid-4-yl)-pyridine having a high bulk density of from about 220 to about 360 g/l, which comprises precipitating said high bulk density crystaline 3-cyano-2-morpholino-5-(pyrid-4-yl)-pyridine from a crude or purified 3-cyano-2-morpholino-5-(pyrid-4-yl)-pyridine starting material that is
   (a) a solution of said starting material in an inorganic or organic acid, and precipitating with a base, or
   (b) a solution of said starting material in a chlorinated hydrocarbon, and precipitating with an aliphatic hydrocarbon, or
   (c) from an aliphatic ester of an aliphatic carboxylic acid of said starting material, and an aliphatic alcohol.

2. The method of claim 1, wherein the starting material is a crude 3-cyano-2-morpholino-5-(pyrid-4-yl)-pyridine.

3. The method of claim 1, wherein, after dissolving the starting material, the solution is treated with an adsorbent.

4. The method of claim 3, wherein said adsorbent is activated charcoal, or silica gel.

5. The method of claim 1, wherein a crystalline, high bulk density 3-cyano-2-morpholino-5-(pyrid-4-yl)-pyridine is precipitated by a base from its acidic solution, at a temperature of from about 15° C. to about 40° C.

6. The method of claim 5, wherein the temperature is about 30° C.

7. The method of claim 1, wherein the base is a solution of an alkali hydroxide, ammonia, or an alkali carbonate.

8. The method of claim 1, wherein the solvent acid is an aqueous solution of a mineral acid, further comprising adding a further amount of the mineral acid to the solution, and precipitating a crystalline 3-cyano-2-morpholino-5-(pyrid-4-yl)-pyridine as the salt of said mineral acid, and separating the precipitate from the aqueous solution.

9. The process of claim 8, further comprising redissolving the separated salt of 3-cyano-2-morpholino-5-(pyrid-4-yl)-pyridine in water, and precipitating it with a base.

10. The process of claim 9, wherein the redissolved solution in water is treated with an adsorbent prior to precipitation with a base.

11. The method of claim 1, wherein a $C_{5-10}$ aliphatic hydrocarbon, or a mixture of such hydrocarbons, is used as the precipitating agent.

12. The method of claim 1, wherein the chlorinated hydrocarbon is chlorinated aliphatic hydrocarbon.

13. The method of claim 11, wherein the chlorinated hydrocarbon is dichloromethane, or chloroform.

14. The method of claim 1, wherein the precipitation takes place from an ester of a $C_{1-3}$ aliphatic carboxylic acid and a $C_{1-4}$ aliphatic alcohol.

15. The method of claim 14, wherein said ester is butyl acetate.

16. The method of claim 14, wherein the recrystallization is carried out while stirring and cooling rapidly and intensively.

* * * * *